United States Patent [19]

Hall

[11] 4,044,761

[45] Aug. 30, 1977

[54] ORTHOPEDIC BANDAGE

[75] Inventor: John Ives Hall, Welwyn Garden City, England

[73] Assignee: Smith & Nephew Research Limited, England

[21] Appl. No.: 659,261

[22] Filed: Feb. 19, 1976

[51] Int. Cl.$^2$ .................................................. A61F 5/04
[52] U.S. Cl. ........................... 128/90; 260/23 R; 260/23 AR; 260/42.29
[58] Field of Search ............. 128/90, 89, 87, 155, 128/156, 157; 260/23 R, 23 AR, 998.11, 42.29

[56] References Cited

U.S. PATENT DOCUMENTS

| 3,683,903 | 8/1972 | Fox et al. ........................ 128/90 |
| 3,692,023 | 9/1972 | Phillips et al. .................. 128/90 |
| 3,751,391 | 8/1973 | Smith ..................... 260/998.11 X |
| 3,882,080 | 5/1975 | Schmitt et al. ........ 260/998.11 X |

Primary Examiner—John D. Yasko
Attorney, Agent, or Firm—Marn & Jangarathis

[57] ABSTRACT

A casting or splinting material in powder form is a mixture of particles of (a) a water-soluble cross-linkable polymer containing carboxylic acid groups, such as polyacrylic acid and (b) zinc oxide and/or one or more zinc salts, this latter material being at least partly coated to reduce its surface reactivity with an organic acid e.g. an aliphatic fatty acid containing from 6 to 20 carbon atoms per molecule. Such material, that can for example be provided as a loading on a Leno gauze, can be made up as a slurry in a volatile organic liquid for coating purposes.

12 Claims, No Drawings

ORTHOPAEDIC BANDAGE

This invention relates to the provision of a water-hardenable composition for medical use. More specifically, it relates to improvements in orthopedic bandages and the manufacture thereof, particularly cast-forming bandages to support or hold in place a broken or otherwise damaged limb.

Conventionally casts or splints are made of an open-weave bandage of Leno gauze carrying a loading of calcium sulphate hemihydrate, that is to say Plaster of Paris. This is in the form of a powdery material, and the bandage is usually provided rolled on an openwork e.g. cruciform core so that for use it is dipped in water for a few seconds (usually 3 or 4 seconds), squeezed, wrapped on the affected limb and allowed to set and eventually to harden. Setting takes from 5 to 10 minutes and hardening takes about 24 hours.

It is conventional with such a bandage that the particles do not block the openings of the gauze, or in other words that the bandage is readily permeable to water even when rolled up. Such a bandage is made by spreading a slurry of Plaster of Paris upon the Leno gauze. This slurry is usually made up in a substantially anhydrous liquid, such as a mixture of industrial methylated spirits and methylene chloride, together with a polymeric additive such as methyl cellulose and/or polyvinyl acetate to provide thickening and to facilitate spreading, binding and general workability.

Plaster casts made using a Plaster of Paris bandage as described above are cheap but tend to make a somewhat heavy cast which has poor water-resistance.

Recently therefore attempts have been made to find an alternative for such material in situations where the disadvantages of the conventional Plaster of Paris bandages outweigh their cheapness.

One prior proposal, described in U.S. patent specification No. 834063, has been the use of a bandage coated with vinyl alkyl ether/maleic anhydride copolymers as a surgical cast. Such materials have the recurring unit:

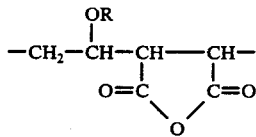

and when hydrolysed by heating in an aqueous environment possess the recurring unit:

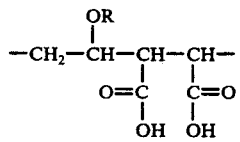

(which unit can be subsequently further esterified on the —OH groups). Where the diacid form of polymer is used it has been proposed to incorporate reactive inorganic compounds such as calcium hydroxide into the mixture so that it reacts and hardens in the presence of water. The particle size of such compound has been found to affect the setting and hardening times.

It is also known that, for example, zinc oxide can be mixed with polyacrylic acid to form a cement, useful as a splinting material or as a dental cement. The exact mechanism of the reaction between these two components is unclear, but it is believed that cross-linking of the polymer by the metal is the major factor. Once again, unduly fast reaction must be avoided, to allow some time for manipulation; in this case this is usually achieved by prior heat treatment of the zinc oxide to deactivate the surface.

The present invention provides a different method of controlling the reaction time and in one aspect consists in water-hardenable powder material comprising a mixture of particles of:

a. a water-soluble crosslinkable polymeric material containing carboxylic acid groups and
b. one or more zinc oxides and/or zinc with at least one weak acid which oxide and/or salt has been at least partially coated with an organic acid to reduce its surface reactivity.

Preferably such a material is in the form of a loading on to a carrier, e.g. a fabric, for example an openwork gauze of the type known as "Leno" gauze. Preferably moreover this material is provided in the form of a roll of the loaded fabric, for example upon an openwork former such as a cruciform former.

The organic acid is usually an aliphatic fatty acid, preferably containing from 6 to 20 carbon atoms per molecule. It can be either saturated or unsaturated. Preferred acids are oleic acid, stearic acid, and lauric acid, but other long chain acids such as myristic acid, palmitic acid, or even arachidic acid may also be used. The amount of organic acid is preferably from 1 to 10 percent by weight in relation to the amount of the zinc oxide used. More preferably from 4 to 7 percent by weight is used.

The particulate inorganic material is usually zinc oxide. Preferably the zinc oxide is of a size range below 1.0 and a useful material made in the vapour phase will have an average particle size of 0.1 to 0.3.

Optionally additional inorganic particulate material can be incorporated. Thus, it may be possible to incorporate a proportion of alumina (e.g. up to 75% of the total inorganic material) although it appears that alumina alone would give too slow a reaction to be useful as a casting material in this context. It may moreover be possible to incorporate a proportion of magnesium oxide into the mixture according to the invention. However, barium compounds should be avoided since they have a tendency to be toxic.

The cross-linkable polymeric material containing carboxylic acid groups can be for example polyacrylic acid, or (preferably) a vinyl methyl ethermaleic acid copolymer in the acid form. Water-soluble materials of the above nature which are capable of cross-linking are well known in the art. Preferably in the solid composition the weight ratios of the polymeric material to the inorganic material range from 1:1 to 2:1 by weight.

In another aspect the present invention provides a method of making a splinting or casting material in which a carrier e.g. a relatively openwork fabric is loaded e.g. coated and/or impregnated with a slurry in a volatile organic liquid of particles of:

a. a watersoluble crosslinkable polymeric material containing carboxylic acid groups and
b. one or more oxides, and/or salts of at least one weak acid of zinc which oxide, and/or salt has been at least partially coated with an organic acid to reduce its surface reactivity;

and the volatile liquid is thereafter removed.

The inorganic particles can be precoated before they are incorporated into the slurry.

Alternatively the solid inorganic material (e.g. the zinc oxide is added to the slurry in an unreacted form and the aliphatic acid is separately added. A preferred mode of operation, especially when zinc oxide is used alone, is to dissolve a minor proportion of the fatty acid in the volatile liquid (e.g. from 10 to 20 percent by weight), to add the insoluble particulate inorganic material such as zinc oxide, to add next the remainder of the fatty acid, and thereafter to add the polymeric material. This ensures that the inorganic material is adequately dispersed throughout the slurry prior to application to the carrier, which can be of any suitable material but is usually a fabric such as Leno gauze.

The organic liquid can be any organic liquid which does not cause gelation and which can be fairly readily removed e.g. by evaporation after the slurry has been applied to the fabric. A much preferred liquid is methylenechloride i.e. $CH_2Cl_2$. Preferably the slurry also contains some thickening agent to improve the workability and applicability to the fabric. It will be particularly valuable if this thickening agent is soluble in both the organic liquid and the water (i.e. which is eventually used when the cast is applied) since in such a case it will improve the workability of the cast. Thus, cellulosic thickening agents are valuable in this context and a preferred cellulosic thickening agent is hydroxypropyl cellulose. In the slurry it can be present in amount up to 10 per cent by weight, and more preferably in amounts up to 5 per cent by weight.

The above material can be used in the same way as the conventional material. That is to say, it can be dipped in water for a few seconds, gently squeezed out with minimal plaster loss, wrapped around the limb, with overlapping edges, up to a thickness of about one quarter of an inch, and smoothed into a suitable contour over the ensuing five minutes or so working time.

The invention will be further described with reference to the following examples.

EXAMPLE 1

1g. of oleic acid was dissolved in 60 ml. of methylene chloride ($CH_2Cl_2$). To this was added 60g. of zinc oxide of particle size 0.22 microns from Durham Raw Materials Ltd. The ensuing slurry was stirred. Thereafter was added a further 3g. of oleic acid, followed by a further 60 ml. of the methylene chloride in which was dissolved 3g. of hydroxypropyl cellulose available under the trade mark Klucel EF from the Hercules Powder Corporation. To the stirred slurry was then added 100g. of a vinylmethyl ether/maleic acid copolymer available under the trade designation of S95 or "CANTREZ" from the General Aniline & Film Corporation.

The thickened slurry thereby produced was spread to give a 50g. (dry weight) coating on Leno gauze carrier 2.7 m; long and 75 mm. wide. A cast formed by dipping the rolled bandage in water and wrapping it around a mandrel gelled, within 5 mins. thereafter set and hardened within 24 hrs. Instron testing was carried out at one inch per minute diametric compression on a 2-inch diameter cast formed from the bandage by winding around a 2-inch mandrel. The compressive force necessary to give 0.15 inch deformation was 1070 g. per gram of bandage.

EXAMPLE 2

Similar bandages to those described in Example 1 but made up with untreated zinc oxide set so quickly that there was no available working time for forming on the mandrel.

The above examples may be compared with the results obtained from a standard cast made from gypsum under the same conditions, the compressive strength of which was only 785 g. Moreover, the subjective water resistance of the casts according to the invention was good.

Various modifications may be made within the scope of the invention as defined above. For instance, a cast could be made using only the inorganic material as the solid e.g. the loading on the bandage, but immersing it in a solution of the polyacrylic acid.

I claim:
1. An orthopedic bandage which comprises:
   a carrier, and
   a water-hardenable powder material loaded on said carrier, said water-hardenable powder material comprised of a mixture of particles of (a) a water-soluble cross-linkable polymeric material containing carboxylic acid groups, and (b) at least one material selected from the group consisting of zinc oxide and zinc salts with at least one weak acid, said at least one material having been at least partially coated with an organic acid to reduce its surface reactivity.
2. The orthopedic bandage as claimed in claim 1 wherein said carrier is Leno gauze.
3. The orthopedic bandage as claimed in claim 1 in which said Leno gauze is in the form of a roll of fabric supported upon an openwork former.
4. The orthopedic bandage as claimed in claim 1 in which said organic acid is an aliphatic fatty acid.
5. The orthopedic bandage as claimed in claim 4 in which said aliphatic fatty acid contains of from 6 to 20 carbon atoms per molecule.
6. The orthopedic bandage as claimed in claim 5 in which said aliphatic fatty acid is selected from the group consisting of oleic acid, stearic acid, lauric acid, myristic acid, palmitic acid and chidic acid.
7. The orthopedic bandage as claimed in claim 4 in which said aliphatic fatty acid is from 1 to 10% by weight in relation to the amount of said at least one material.
8. The orthopedic bandage as claimed in claim 1 in which said at least one material is zinc oxide of particle size below 1.0 microns.
9. The orthopedic bandage as claimed in claim 1 and further including particulate material selected from the group consisting of alumina and magnesium oxide.
10. The orthopedic bandage as claimed in claim 1 in which said cross-linkable polymeric material is a polyacrylic acid.
11. The orthopedic bandage as claimed in claim 1 in which said cross-linkable polymeric material is a vinylmethylether/maleic acid copolymer in the acid form.
12. The orthopedic bandage as claimed in claim 1 in which the weight ratio of said polymeric material to said at least one material is from 1:1 to 2:1.

* * * * *